US008299272B2

(12) United States Patent
Miura et al.

(10) Patent No.: US 8,299,272 B2
(45) Date of Patent: *Oct. 30, 2012

(54) PROCESS FOR PRODUCTION OF FUSED RING COMPOUND

(75) Inventors: Masahiro Miura, Suita (JP); Tetsuya Satoh, Suita (JP); Hiroyuki Watanabe, Suita (JP); Masato Ueda, Tsukuba (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 985 days.

This patent is subject to a terminal disclaimer.

(21) Appl. No.: 12/282,065

(22) PCT Filed: Mar. 9, 2007

(86) PCT No.: PCT/JP2007/054685
§ 371 (c)(1),
(2), (4) Date: Oct. 28, 2008

(87) PCT Pub. No.: WO2007/105638
PCT Pub. Date: Sep. 20, 2007

(65) Prior Publication Data
US 2009/0156832 A1    Jun. 18, 2009

(30) Foreign Application Priority Data

Mar. 10, 2006    (JP) .............................. P2006-066555

(51) Int. Cl.
*C07D 333/00*    (2006.01)
*C07D 495/00*    (2006.01)
*C07D 409/00*    (2006.01)

(52) U.S. Cl. ........................................... 549/43; 549/59
(58) Field of Classification Search ........................ None
See application file for complete search history.

(56) References Cited

FOREIGN PATENT DOCUMENTS

| JP | 2-015079 A | 1/1990 |
|---|---|---|
| JP | 2000-076640 A | 3/2000 |
| JP | 2004-269519 A | 9/2004 |
| JP | 2004-339516 A | 12/2004 |
| WO | 03/072581 A1 | 9/2003 |

OTHER PUBLICATIONS

Dougherty, TK. Anomaly in Palladium-Catalyzed Phenylethynylation of 2,2'-Dihalobiphenyls: Formation of Alkylidenefluorenes. J. Org. Chem. 1983, vol. 48, pp. 5274.*
Larock, RC. Palladium-catalyzed Annulation of Alkynes. Top. Organomet. Chem. 2005, vol. 14, pp. 147-182.*
Larock, RC. Carbopalladation of Nitriles: Synthesis of 3,4-disubstituted 2-aminonaphthalenes and 1,3-benzoxazine Derivatives by the Palladium-Catalyzed Annulation of Alkynes by (2-iodophenyl) acetonitrile. J. Org. Chem. 2003, vol. 68, p. 339.*
Hudkins, RL. Synthesis and Mixed Lineage Kinase Activity of Pyrrolocarbazole and Isoindolone Analogs of (+)K-252a. J. Med. Chem. 2007, vol. 50, p. 435, scheme 5a.*
Merlic, CA. Synthesis of Indolocarbazoles via Sequential Palladium Catalyzed Cross-Coupling and Benzannulation Reactions. Tetrahedron Letters. 1997, vol. 38, p. 7663.*
T.K. Doughtery et al. "Anomaly in Palladium-Catalyzed Phenylethynylation of 2,2'-Dihalobiphenyls: Formation of Alkylidenefluorenes", J. Org. Chem., 48, 1983, p5273-p5280.
Merlic, Craig A. et al., Synthesis of indolocarbazoles via sequential palladium catalyzed cross-coupling and benzannulation reactions, Tetrahedron Letters, (1997), 38 (44), pp. 7661-7664.
Tsuchimoto, T. et al., Easy access to aryl- and heteroaryl-annulated [a] carbazoles by the indium-catalyzed reaction of 2-arylindoles with propargyl ethers, Angewandte Chemie, International Edition, (2005), vol. 44, No. 9, pp. 1336-1340. Wiersema, Allert K. et al., Thiophene analog of fluorene. IV. Unusual behavior of a cyclopentadithiophenone in the reaction with dienophiles, Acta Chemica Scandinavica, 1974-1974, (1970), 24(7), pp. 2653-2655.
M.J. Janssen et al., "The Synthesis, Oxidation, and Electronic Spectra of Four Dithienothiophenes", J. Org. Chem., vol. 36, No. 12, (1971), pp. 1645-1648.
X. Li et al., "A Highly-Stacked Organic Semiconductor for Thin Film Transistors Based on Fused Thiophenes", J. Am. Chem. Soc., vol. 120, (1998), pp. 2206-2207.
P. Coppo et al., "Synthesis, solid state structure and polymerisation of a fully planar cyclopentadithiophene", Chem. Commun., (2003), pp. 2548-2549.

(Continued)

*Primary Examiner* — Rita Desai
*Assistant Examiner* — Ben S Michelson
(74) *Attorney, Agent, or Firm* — Sughrue Mion, PLLC

(57) ABSTRACT

It is an object of the present invention to provide a method for manufacturing a fused ring compound, with which a fused ring compound that has excellent charge transport property and that has excellent solubility in solvents can be obtained efficiently. The method of the present invention for manufacturing a fused ring compound involves reacting a compound expressed by the following General Formula (1a) and a compound expressed by the following General Formula (1b) in the presence of an amine and a metal complex catalyst:

[C1]

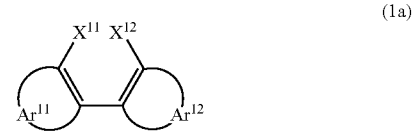

(1a)

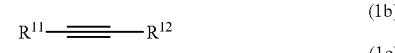

(1b)

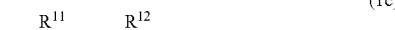

(1c)

(where $Ar^{11}$ and $Ar^{12}$ are each independently an atom group constituting an aromatic ring or a heterocyclic ring; $X^{11}$ and $X^{12}$ are each independently a hydrogen atom or a halogen atom, and at least one is a halogen atom; and $R^{11}$ and $R^{12}$ are each independently a hydrogen atom, an alkyl group, an alkoxy group, an alkylthio group, an alkylamino group, an alkoxycarbonyl group, an aryl group, a heterocyclic group, or a cyano group, provided that at least one of $R^{11}$ and $R^{12}$ is not a hydrogen atom).

5 Claims, No Drawings

OTHER PUBLICATIONS

W. Archer et al., "Electro philic Aromatic Substitution. Part 34.1 Partial Rate Factors for Detritiation of Dithieno[1,2-b :4,3-b']benzene, Dithieno[1,2-b :3,4-b']benzene, and Dithieno[2,1-b :3,4-b']benzene", J. Chem. Soc. Perkin Trans. II, (1983), pp. 813-819.

S. Yoshida et al., "Novel Electron Acceptors Bearing a Heterquinonoid System. 4.1 Syntheses, Properties, and Charge-Transfer Complexes of 2,7-Bis(dicyanomethylene)-2,7-dihydrobenzo[2,1-b:3,4-b']dithiophene, 2,7-Bis(dicyanomethylene)-2,7-dihydrobenzo[1,2-b:4,3-b']dithiophene, and 2,6-Bis(dicyanomethylene)-2,6-dihydrobenzo[1,2-b:4,5-b']dithiophene", J. Org. Chem., vol. 59, (1994), pp. 3077-3081.

K. Kanno et al., "Chromium-Mediated Synthesis of Polycyclic Aromatic Compounds from Halobiaryls", Organic Letters, vol. 7, No. 24, (Sep. 14, 2005), pp. 5453-5456.

Department of Chemistry, Imperial College, "Palladium catalysed cross coupline reactions" [online]. Available from http://web.archive.org/web/19990224202038/http://www.ch.ic.ac.uk/local/organic/4-palladium.html [Published Feb. 24, 1999. Accessed Sep. 27, 2010].

Ricard C. Larock, Palladium-Catalyzed Annulation of Alkynes, Topics in Organometallic Chemistry, vol. 14, 2005, pp. 147-182.

* cited by examiner

US 8,299,272 B2

PROCESS FOR PRODUCTION OF FUSED RING COMPOUND

TECHNICAL FIELD

This invention relates to a method for manufacturing a fused ring compound.

BACKGROUND ART

Organic semiconductor materials have been the subject of much research in recent years because they can be applied to a variety of organic thin-film devices, such as organic EL (electroluminescence) devices, organic transistors, organic solar cells, and light sensors. If excellent performance is to be obtained in these applications, the organic semiconductor material needs to have high charge (electron or hole) transport property. To obtain high charge transport property, it is important to use a molecule with wide π conjugation in the organic semiconductor material, for the molecular packing to be good, and to increase molecular interaction.

An example of an organic semiconductor material that affords high charge transport property is a fused ring compound in which a plurality of aromatic rings or heterocyclic rings are bonded with conjugation, and polymers of such compounds. Of these, thiophene-containing compounds that include a plurality of thiophene rings, and polymers of these compounds, are known to have high charge transport property (see Patent Document 1). As for methods for manufacturing fused ring compounds, a method in which a plurality of thiophene rings are subjected to planar crosslinking (see Non-Patent Documents 1 to 3) has been disclosed as a method for manufacturing a thiophene-containing compound, for example. A method in which a bithiophene ring is crosslinked with vinylene is also known (see Non-Patent Documents 4 and 5).

Patent Document 1: Japanese Laid-Open Patent Application 2004-339516
Non-Patent Document 1: M. J. Janssen et al., "*J. Org. Chem.*," 1971, Vol. 36, 1645.
Non-Patent Document 2: X. Li et al., "*J. Am. Chem. Soc.*," 1998 Vol. 120, 2206.
Non-Patent Document 3: P. Coppo et al., "*Chem. Commun.*," 2003, 2548.
Non-Patent Document 4: W. Archer et al., "*J. Chem. Soc. Perkin Trans. 2*," 1983, 813.
Non-Patent Document 5: S. Yosida et al., "*J. Org. Chem.*," 1994, Vol. 59, 3077.

DISCLOSURE OF THE INVENTION

Problem to be Solved by the Invention

With the above-mentioned manufacturing methods of prior art, however, it still tends to be difficult to efficiently obtain a fused ring compound with excellent charge transport property. Also, in the formation of an organic thin film, fused ring compounds are often used after being dissolved in a solvent, but the fused ring compounds obtained with the above methods often had poor solubility in solvents.

In view of this, the present invention was conceived in light of this situation, and it is an object thereof to provide a method for manufacturing a fused ring compound, with which a fused ring compound with excellent charge transport property and with excellent solubility in solvents can be obtained efficiently.

Means for Solving the Problem

To achieve the stated object, the method of the present invention for manufacturing a fused ring compound involves reacting a compound expressed by the following General Formula (1a) and a compound expressed by the following General Formula (1b) in the presence of an amine and a metal complex catalyst, thereby obtaining a fused ring compound expressed by the following General Formula (1c):

[C1]

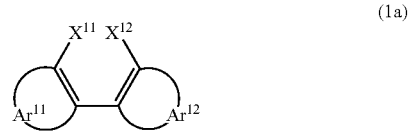

(1a)

(1b)

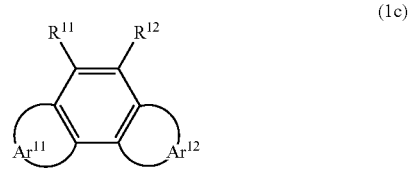

(1c)

(where $Ar^{11}$ and $Ar^{12}$ are each independently an atom group constituting an aromatic ring that may have a substituent or a heterocyclic ring that may have a substituent; $X^{11}$ and $X^{12}$ are each independently a hydrogen atom or a halogen atom, provided that at least one of $X^{11}$ and $X^{12}$ is a halogen atom; and $R^{11}$ and $R^{12}$ are each independently a hydrogen atom, an alkyl group, an alkoxy group, an alkylthio group, an alkylamino group, an alkoxycarbonyl group, an aryl group that may have a substituent, a heterocyclic group that may have a substituent or a cyano group, provided that at least one of $R^{11}$ and $R^{12}$ is not a hydrogen atom).

With the manufacturing method discussed above, a fused ring compound is produced merely by reacting the compound of General Formula (1a) with the compound of General Formula (1b), so a fused ring compound can be obtained very efficiently. Also, the resulting fused ring compound has a structure with wide π conjugation in which three aromatic ring structures are fused, which means that high charge transport property is exhibited when an organic thin film or the like is formed. Furthermore, because this fused ring compound has a structure in which a substituent is introduced into the benzene ring structure in the center, its solubility in solvents is also good.

In particular, with the method of the present invention for manufacturing a fused ring compound, a compound expressed by the following General Formula (2a) and a compound expressed by the following General Formula (2b) are reacted in the presence of an amine and a metal complex catalyst, thereby obtaining a fused ring compound expressed by the following General Formula (2c). The fused ring compound obtained by such a process especially exhibits high charge transport property.

[C2]

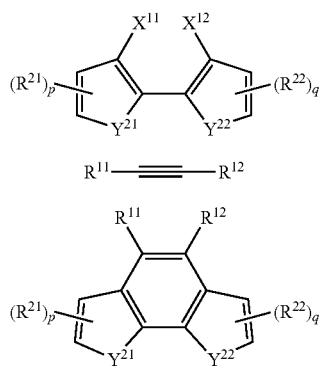

(where $X^{11}$, $X^{12}$, $R^{11}$ and $R^{12}$ are defined the same as above; $R^{21}$ and $R^{22}$ are each independently a monovalent group; p and q are each independently an integer from 0 to 2; and $Y^{21}$ and $Y^{22}$ are each independently a divalent group expressed by the following General Formula (3a), (3b), (3c), (3d), (3e), (3f), (3g), (3h) or (3i);

[C3]

here, $R^{31}$, $R^{32}$, $R^{33}$, and $R^{34}$ are each independently a hydrogen atom or a monovalent group, and $R^{33}$ and $R^{34}$ may be bonded together to form a ring)

With the compounds expressed by General Formulas (2a) and (2c), $Y^{21}$ and $Y^{22}$ are preferably divalent groups expressed by General Formula (3a). This affords even better charge transport property in the resulting fused ring compound. Also, such a compound expressed by General Formula (2a) has the advantages of being relatively easy to synthesize and using readily available raw materials.

$R^{11}$ and $R^{12}$ are preferably each independently a $C_1$ to $C_{10}$ alkyl group. This affords even better solubility of the resulting fused ring compound in solvents.

Further, at least one of $X^{11}$ and $X^{12}$ is preferably an iodine atom. This will facilitate the occurrence of a reaction between a compound expressed by General Formula (1a) or (2a) and a compound expressed by General Formula (1b) or (2b), and will allow a compound expressed by General Formula (1c) or (2c) to be obtained even more efficiently.

Further, the amine is preferably a trialkylamine. The metal complex catalyst is preferably a metal complex catalyst that contains Pd. This will allow a fused ring compound to be obtained even more efficiently.

Effect of the Invention

The present invention provides a method for manufacturing a fused ring compound, with which a fused ring compound that has excellent charge sport property and that has excellent solubility in solvents can be obtained efficiently.

BEST MODE FOR CARRYING OUT THE INVENTION

Preferred embodiments of the present invention will now be described in detail.

With the method of the present invention for manufacturing a fused ring compound, a compound expressed by General Formula (1a) and a compound expressed by General Formula (1b) are reacted in the presence of an amine and a metal complex catalyst, thereby obtaining a fused ring compound expressed by General Formula (1c).

With this manufacturing method, a reaction occurs between the groups expressed by $X^{11}$ and $X^{12}$ in the compound of General Formula (1a) and the triple bond in the compound of General Formula (1b), and this reaction crosslinks two aromatic rings or heterocyclic rings ($Ar^1$ and $Ar^2$) in the compound of General Formula (1a), and a six-member ring structure is formed between these. Furthermore, this reaction is preferably conducted in an inert gas atmosphere of nitrogen, argon, or the like.

With the manufacturing method of this embodiment, a fused ring compound expressed by General Formula (1) is obtained by bringing about the reaction expressed by the following reaction formula, although there are no particular restrictions imposed.

[C4]

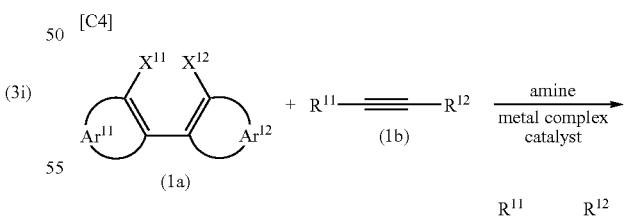

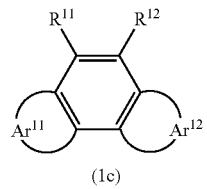

$X^{11}$ and $X^{12}$ in General Formula (1a) are each independently a hydrogen atom or a halogen atom, and at least one is a halogen atom, but it is preferable for both of them to be halogen atoms. Of these, at least one of $X^{11}$ and $X^{12}$ is preferably an iodine atom, and preferably both of them are iodine atoms. If $X^{11}$ and $X^{12}$ are iodine atoms, there will be a tendency for the above-mentioned reaction to occur much more readily.

$Ar^{11}$ and $Ar^{12}$ in General Formulas (1a) and (1c) are each independently an atom group constituting an aromatic ring or heterocyclic ring along with a double bond to which these are bonded. The aromatic rings or heterocyclic rings may further have a substituent $Ar^{11}$ and $Ar^{12}$ preferably have in their structure a multiple bond capable of conjugating with the double bond to which these are bonded.

The aromatic ring that makes up $Ar^{11}$ and $Ar^{12}$ preferably has a carbon number of 6 to 60 (hereinafter abbreviated as $C_6$ to $C_{60}$; the same applies hereinafter), and even more preferable is $C_6$ to $C_{20}$. Both a single ring and a fused ring can be applied as the aromatic ring. A benzene ring is an example of a single ring, while naphthalene, anthracene, pyrene, perylene, and fluorene are examples of fused rings.

The heterocyclic ring is preferably $C_4$ to $C_{60}$, and even more preferably $C_4$ to $C_{20}$. Both a single ring and a fused ring can be applied as the heterocyclic ring here. Of these, a single ring is preferable as the heterocyclic ring, and a heterocyclic ring having a five-member ring structure is even more preferable.

Examples of the substituent that may be had by $Ar^{11}$ and $Ar^{12}$ include a halogen atom, a saturated or unsaturated hydrocarbon group, an aryl group, an alkoxy group, an aryloxy group, a heterocyclic group, an amino group, a nitro group, and a cyano group. This substituent is preferably a polymerizable functional group. It is even better if $Ar^{11}$ and $Ar^{12}$ both have a polymerizable functional group, because it will be easier to obtain a polymer having superior charge transport property from a fused ring compound. Examples of substituents that may be had by $Ar^{11}$ and $Ar^{12}$ are the same as the groups expressed by $R^{21}$ and $R^{22}$ in General Formulas (2a) and (2c) above.

Also, $R^{11}$ and $R^{12}$ in General Formulas (1b) and (1c) are each independently a hydrogen atom, an alkyl group, an alkoxy group, an alkylthio group, an alkylamino group, an alkoxycarbonyl group, an aryl group that may have a substituent, or a heterocyclic group that may have a substituent or a cyano group. Preferably, at least one of $R^{11}$ and $R^{12}$ is not a hydrogen atom, and preferably neither of them is a hydrogen atom. "Alkyl group" here includes linear, branched, and cyclic groups. Also, some or all of the hydrogen atoms of the above-mentioned functional groups may be substituted with halogen atoms (and particularly fluorine atoms).

The alkyl group here is preferably a $C_1$ to $C_{20}$ group. Examples of such alkyl groups include a methyl group, an ethyl group, a n-propyl group, an iso-propyl group, a n-butyl group, an iso-butyl group, a tert-butyl group, a pentyl group, a hexyl group, a heptyl group, an octyl group, a nonyl group, a decyl group, a lauryl group, a cyclopropyl group, a cyclopentyl group, a cyclohexyl group, a cycloheptyl group, a cyclooctyl group a cyclononyl group, and a cyclododecyl group. Of these, $C_1$ to $C_{10}$ alkyl groups are preferable; for example, a pentyl group, a hexyl group, an octyl group, a decyl group, or a cyclohexyl group is favorable.

The alkoxy group, alkylthio group, alkylamino group, and alkoxycarbonyl group are preferably one in which the alkyl groups had by these are $C_1$ to $C_{20}$ alkyl groups. Examples of these $C_1$ to $C_{20}$ alkyl groups are the same as those listed above.

The aryl group that may have a substituent is preferably a $C_6$ to $C_{60}$ group. Examples include a phenyl group, a phenyl group having a $C_1$ to $C_{12}$ alkoxy group, a phenyl group having a $C_1$ to $C_{12}$ alkyl group, a 1-naphthyl group, and a 2-naphthyl group. Of these, $C_6$ to $C_{20}$ aryl groups are preferable, and a phenyl group having a $C_1$ to $C_{12}$ alkoxy group or a phenyl group having a $C_1$ to $C_{12}$ alkyl group is particularly favorable.

The heterocyclic group that may have a substituent is preferably a $C_4$ to $C_{60}$ group. Examples include a thienyl group, a thienyl group having a $C_1$ to $C_{12}$ alkyl group, a pyrrolyl group, a furyl group, a pyridyl group, and a pyridyl group having a $C_1$ to $C_{12}$ alkyl group. Of these, a $C_4$ to $C_{20}$ heterocyclic group is preferable, and it is particularly favorable to use a thienyl group, a thienyl group having a $C_1$ to $C_{12}$ alkyl group, a pyridyl group, or a pyridyl group having a $C_1$ to $C_{12}$ alkyl group. The term "heterocyclic group" refers to an organic group having a cyclic structure, in which at least one of the atoms that make up the ring is a hetero atom.

Of the above, $R^{11}$ and $R^{12}$ are preferably each independently a $C_1$ to $C_{20}$ alkyl group or an aryl group that may have a $C_6$ to $C_{60}$ substituent, and a $C_1$ to $C_{10}$ alkyl group or an aryl group that may have a $C_6$ to $C_{20}$ substituent is more preferable, with a $C_1$ to $C_{10}$ alkyl group being particularly favorable.

The amine used to manufacture the fused ring compound can be an alkylamine, an arylamine, or the like, without any particular restrictions imposed. A fused ring compound can be obtained efficiently by conducting a reaction between the compound of General Formula (1a) and the compound of General Formula (1b) in the presence of an amine. Also, in the reaction between the compound of General Formula (1a) and the compound of General Formula (1b), there may be by-products of a structure in which multiple bonds that $R^{11}$ and $R^{12}$ do not originally have are introduced to these groups in the structure expressed by General Formula (1c), but in the present invention, the amount of such by-products is greatly reduced by conducting the reaction in the presence of an amine.

The amine is preferably one in which at least one alkyl group is bonded to the nitrogen atom of the amine, favorable examples of which include trialkylamines, dialkylarylamines, and alkyldiarylamines. Examples of favorable alkyl groups are the same as those listed for $R^{11}$ and $R^{12}$ above, but a $C_1$ to $C_{20}$ alkyl group is preferable.

This amine is preferably one in which carbons adjacent to the nitrogen atom have at least one hydrogen atom, that is, one having a structure expressed by N—CHx (x=1 to 3), or one in which carbons adjacent to the nitrogen atom have at least two hydrogen atoms, that is, one having a structure expressed by N—CHx (x=2 or 3). With an amine having a structure such as this, the production of by-products is suppressed while a fused ring compound can be obtained at a higher yield.

Of these, a trialkylamine in which three alkyl groups are bonded to the nitrogen atom is preferable because this effect will be particularly pronounced. Specific examples of trialkylamines include trimethylamine, triethylamine, diisopropylethylamine, tri-n-propylamine, tri-n-butylamine, dicyclohexylmethylamine, and cyclohexyldimethylamine.

In the reaction between the compound of General Formula (1a) and the compound of General Formula (1b), the amine is preferably used in an amount of 200 to 400 mol % with respect to the compound of General Formula (1a) serving as a raw material, and an amount of 240 to 300 mol % is even better. It may be difficult to obtain a fused ring compound at a good yield if the amount in which the amine is used is either less than 200 mol % or more than 400 mol % with respect to the compound of General Formula (1a). In the synthesis of the fused ring compound, a basic group other than an amine may be used along with an amine.

Examples of the metal complex catalyst include a palladium complex, a nickel complex, a platinum complex, a ruthenium complex, a rhodium complex, and an iridium complex. Of these, a palladium complex or a nickel complex is preferable, and a palladium complex is particularly favorable. There are no particular restrictions on the palladium complex, but one capable of promoting a coupling reaction of an aromatic halide is preferable. Examples of such palladium complexes include divalent palladium complexes, and palladium complexes having electron donative ligands.

Examples of divalent palladium complexes include palladium acetate, palladium chloride, sodium palladate, and potassium palladate, with palladium acetate being preferable. Examples of palladium complexes having electron donative ligands include tetrakis(triphenylphosphine) palladium, dichlorobis(triphenylphosphine) palladium, and tris(dibenzylideneacetone) palladium, with tetrakis(triphenylphosphine) palladium being preferable.

The metal complex catalyst may be one of the above used singly, or a plurality may be combined and used together. The metal complex catalyst is preferably used in an amount of 0.01 to 50 mol %, and more preferably 0.5 to 20 mol %, and even more preferably 1 to 15 mol %, with respect to the compound expressed by General Formula (1a) serving as a raw material.

The reaction of the compound of General Formula (1a) and the compound of General Formula (1b) can also be conducted in a solvent. This solvent is preferably inert with respect to the reaction. Examples include toluene, dimethylformamide (DMF), N-methyl-2-pyrrolidone (NMP), tetrahydrofuran (THF), dioxane, isopropyl alcohol, acetonitrile, and pinacolone. Of these, toluene, NMP, or dioxane is preferred. There are no particular restrictions on the amount in which the solvent is used, but for example, the amount is preferably 1 to 100 times, and more preferably 2 to 30 times, the weight of the compound expressed by General Formula (1a) serving as a raw material.

There are no particular restrictions on how long the reaction lasts, but it can be concluded at the point when either the compound of General Formula (1a) or the compound of General Formula (1b) runs out. The reaction may also be concluded at the point when the fused ring compound that is the product reaches a certain amount. It takes about 0.5 to 200 hours from the start of the reaction until its conclusion. The reaction temperature may be suitably set between −50 and 300° C., and about 50 to 150° C. is preferable.

The above-mentioned method for manufacturing a fused ring compound can be applied particularly favorably when $Ar^{11}$ and $Ar^{12}$ are each an atom group constituting a heterocyclic ring having a five-member ring structure. More specifically, a fused ring compound expressed by General Formula (2c) is preferably obtained by reacting a compound expressed by General Formula (2a) with a compound expressed by General Formula (2b). In this case, not only is a fused ring compound as the product obtained especially efficiently, but a fused ring compound having particularly good charge transport property is obtained. $X^{11}$, $X^{12}$, $R^{11}$, and $R^{12}$ in these formulas are defined the same as above.

The groups expressed by $Y^{21}$ and $Y^{22}$ in the compounds expressed by General Formulas (2a) and (2c) are each independently a divalent group expressed by General Formula (3a), (3b), (3c), (3d), (3e), (3f), (3g), (3h), or (3i) (hereinafter referred to as (3a) to (3i)). $R^{31}$ to $R^{34}$ in these divalent groups are each independently a hydrogen atom or a monovalent group. $R^{33}$ and $R^{34}$ may be bonded together to form a ring. Examples of the monovalent group here include the same groups as the above-mentioned $R^{11}$ and $R^{12}$, as well as halogen atoms. The group expressed by (3h) has an asymmetrical structure, but there are no particular restrictions on the direction in which the bond chain is bonded.

Of the above, $Y^{11}$ and $Y^{12}$ are preferably a divalent group expressed by (3a), (3b), (3c), (3h), or (3i), and more preferably a divalent group expressed by (3a), (3b), (3c), or (3i). When $Y^{11}$ and $Y^{12}$ are each a divalent group expressed by (3a), (3b), or (3c), the five-member ring structure that includes these (two five-member rings bonded to a benzene ring) is a thiophene ring, a furan ring, or a pyrrole ring. It is particularly favorable for $Y^{11}$ and $Y^{12}$ to be divalent groups expressed by (3a) (that is, for the ring structure to be a thiophene ring) because good charge transport property will be obtained.

$R^{21}$ and $R^{12}$ in the compounds expressed by General Formulas (2a) and (2c) are each independently a monovalent group, and p and q are each independently a number from 0 to 2. If p or q is 2, the plurality of $R^{21}$ or $R^{22}$ groups may be the same or different.

Examples of $R^{21}$ and $R^{22}$ include an alkyl group, an alkoxy group, a fluoroalkyl group, a fluoroalkoxy group, an aryl group, an arylamino group, and a heterocyclic group. Of these, an alkyl group or an aryl group is preferable. Further, $R^{21}$ and $R^{22}$ are preferably changed appropriately as dictated by the carrier to be transported by the organic thin film that includes the fused ring compound. For instance, if the hole transport property of the organic thin film is to be increased, then an arylamino group or other electron donative group is preferred, but from the standpoint of improving electron transport property, a fluoroalkyl group, fluoroalkoxy group, or other electron attractive group is preferred.

Polymerizable functional groups are also examples of $R^{21}$ and $R^{22}$. In particular, if one or both of $R^{21}$ and $R^{22}$ are polymerizable functional groups, the fused ring compound expressed by General Formula (2c) will also be favorable as a raw material for a polymer having even better charge transport property. The term "polymerizable functional group" here refers to a group that can produce a bond by reacting with another polymerizable functional group.

Examples of polymerizable functional groups include a halogen atom, an alkyl sulfonate group, an aryl sulfonate group, an arylalkyl sulfonate group, an alkylstannyl group, an arylstannyl group, an arylalkylstannyl group, a boric acid ester group, a sulfonium methyl group, a phosphonium methyl group, a phosphonate methyl group, a monohalogenated methyl group, a boric acid group, a formyl group, and a vinyl group. Of these, a halogen atom, an alkylstannyl group, and a boric acid ester group are preferable. The combination of polymerizable functional groups is preferably set according to the reaction that will be produced during polymerization.

The fused ring compound obtained by the manufacturing method discussed above can form an organic thin film with excellent charge transport property, either directly or after first being polymerized. This organic thin film is able to efficiently transport holes or electrons injected from an electrode or the like, or charges generated by optical absorption, etc., and can be applied to various kinds of electrical devices that make use of organic thin films (organic thin film devices). Examples of organic thin film devices in which such an organic thin film can be applied include organic thin film transistors, solar cells, light sensors, organic electroluminescent (EL) devices, organic memories, photorefractive devices, space light modulators, and imaging devices.

WORKING EXAMPLES

The present invention will now be described in further detail by giving working examples, but the present invention is not limited to or by these examples.

(Measurement Conditions)

In the synthesis and working examples that follow, the various analyses and so forth were conducted under the following conditions. First, the nuclear magnetic resonance (NMR) spectrum was measured using a JNM-GSX-400 made by JEOL. Gas chromatography-mass spectrometry (GC-MS) was conducted using a QP-5050 made by Shimadzu. High resolution mass spectrometry (HRMS) was conducted using a JMS-DX-303 made by JEOL. Gas chromatography (GC) was performed by using a GC-8A made by Shimadzu and mounting on it a glass column (inside diameter of 2.6 mm and length of 1.5 mm) packed with OV-17 silicon and made by GL Science. Wako Gel C-200 made by Wako Pure Chemical Industries was used for the silica gel in gas chromatography separation.

Synthesis Example 1

Synthesis of 3,3'-diiodo-2,2'-bithiophene

First, 3,3'-dibromo-2,2'-bithiophene as the starting raw material was synthesized by referring to a reference publication (M. Hong and H. Wei, *J. Org. Chem.*, 2000, 65, 3895). This was then used to perform a halogen exchange reaction and synthesize 3,3'-diiodo-2,2'-bithiophene. Specifically, first 3,3'-dibromo-2,2'-bithiophene (2.7 g (7 mmol)) was put in a 300 mL three-neck flask and dissolved in diethyl ether (70 mL). Next, the inside of the reaction vessel was replaced with nitrogen and cooled to −78° C. Butyllithium (10.3 mL (15.4 mmol) of a 1.5 M hexane solution) was then added, and the system was stirred for 1 hour. Further, iodine (3.9 g (15.4 mmol)) dissolved in diethyl ether was added and the system was reacted under stirring for 1 hour at room temperature.

After the reaction, diethyl ether (approximately 50 mL) was added to the solution, and the system was washed with a saturated sodium thiosulfate aqueous solution. After this, the organic layer was dried with sodium sulfate, and then filtered with celite. The solvent was then distilled off from the filtrate, and the resulting solid was recrystallized with hexane and toluene, which gave the targeted substance (3,3'-diiodo-2,2'-bithiophene; the compound expressed by the following chemical formula (5a)) in the form of a white solid (1.9 g; yield of 65%). The melting point of the obtained white solid was measured and found to be 148° C. (Published value: 149.5-151° C.; S. Gronowitz, V. Vilks, *Arkiv Kemi*, 1963, 21, 191.)

[Manufacture of Fused Ring Compound]

In the working examples that follow, reactions expressed by the following reaction formulas were conducted, and the yields were calculated for the fused ring compound expressed by the following General Formula (5c) as the target compound and for the compound expressed by the following General Formula (5d) as by-product. The yield in every case was calculated on the basis of the result obtained by

[C5]

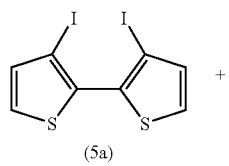

(5a)

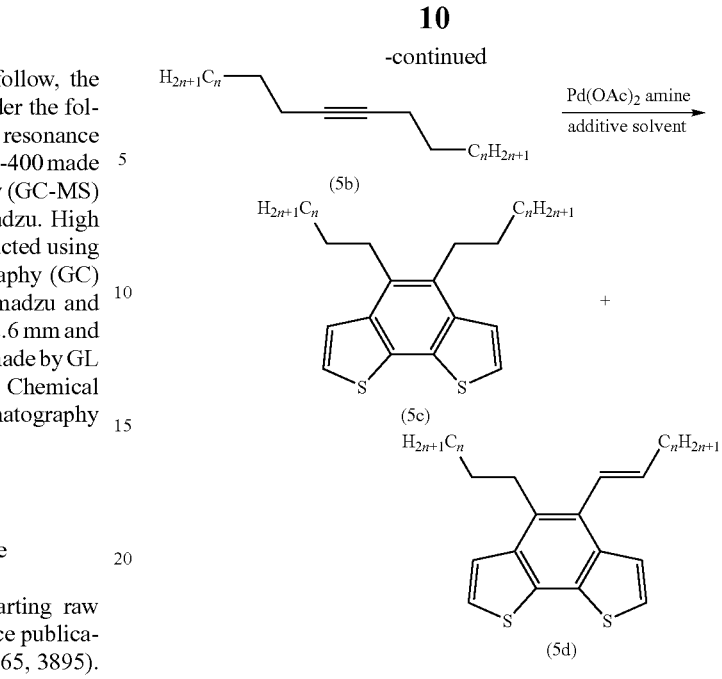

Working Example 1

Synthesis of 4,5-di(n-propyl)benzo[2,1-b:3,4-b']dithiophene 3,3'-diiodo-2,2'-bithiophene (84 mg (0.2 mmol)), palladium(II) acetate ($Pd(OAc)_2$, 4.5 mg (0.02 mmol)), 4-octyne (66 mg (0.6 mmol)), N,N-dicyclohexylmethylamine ($Cy_2MeN$, 117 mg (0.6 mmol)), and N,N-dimethylformamide (2.5 mL) were added to a 20 mL two-neck flask, the inside of the reaction vessel was replaced with nitrogen and heated to 100° C., and the system was reacted under stirring. 4 hours later, it was confirmed by GC and GC-MS analysis that 4,5-di(n-propyl)benzo[2,1-b:3,4-b']dithiophene had been produced substantially quantitatively (a yield of over 99%) in the reaction mixture.

Next, diethyl ether (approximately 20 mL) was added to the resulting reaction solution, and the system was washed with water. After this, the organic layer was dried with sodium sulfate, and then filtered with celite. The solvent was then distilled off from the filtrate, after which the remaining liquid was refined by silica gel column chromatography using hexane as the developing solvent, which gave the targeted substance, in which n=1 in General Formula (5c), in the form of an oily substance (46 mg, isolation yield of 84%). No compound expressed by General Formula (5d) was produced.

The product thus obtained was measured by $^1$H-NMR and HRMS, the results of which were as follows.

$^1$H-NMR (400 MHz, $CDCl_3$, ppm): δ 7.45 (d, J=5.5 Hz, 2H), 7.35 (d, J=5.5 Hz, 2H), 3.01 (m, 4H), 1.74-1.64 (m, 4H), 1.07 (t, J=7.3 Hz, 6H).

HRMS (EI): m/z 274.0847 (the value obtained by measurement with $C_{16}H_{18}S_2$ was 274.0850)

Working Example 2

Synthesis of 4,5-di(n-propyl)benzo[2,1-b:3,4-b']dithiophene

The same reaction as in Working Example 1 was conducted, except that tributylamine ($Bu_3N$, 111 mg (0.6 mmol))

was used instead of N,N-dicyclohexylmethylamine, and the reaction time was changed to 8 hours. After the reaction, it was confirmed by GC and GC-MS analysis that the target substance had been produced substantially quantitatively (a yield of over 99%) in the reaction mixture. No compound expressed by General Formula (5d) was produced.

Working Example 3

Synthesis of 4,5-di(n-propyl)benzo[2,1-b:3,4-b'] dithiophene

The same reaction as in Working Example 1 was conducted, except that cyclohexyldimethylamine (CyMe$_2$N, 76 mg (0.6 mmol)) was used instead of N,N-dicyclohexylmethylamine, and the reaction time was changed to 8 hours. After the reaction, it was confirmed by GC and GC-MS analysis that the target substance had been produced at a yield of 92% in the reaction mixture. No compound expressed by General Formula (5d) was produced.

Working Example 4

Synthesis of 4,5-di(n-propyl)benzo[2,1-b:3,4-b'] dithiophene

The same reaction as in Working Example 1 was conducted, except that diisopropylethylamine (i-Pr$_2$EtN, 78 mg (0.6 mmol)) was used instead of N,N-dicyclohexylmethylamine, and the reaction time was changed to 6 hours. After the reaction, it was confined by GC and GC-MS analysis that the target substance had been produced at a yield of 88% in the reaction mixture. No compound expressed by General Formula (5d) was produced.

Working Example 5

Synthesis of 4,5-di(n-pentyl)benzo[2,1-b:3,4-b'] dithiophene 3,3'-diiodo-2,2'-bithiophene (84 mg (0.2 mmol)), Pd(OAc)$_2$ (2.2 mg (0.01 mmol)), 6-dodecyne (40 mg (0.24 mmol)), N,N-dicyclohexylmethylamine (94 mg (0.48 mmol)), and N,N-dimethylformamide (2.5 mL) were added to a 20 mL two-neck flask, the inside of the reaction vessel was replaced with nitrogen and heated to 130° C., and the system was reacted under sting.

3 hours later, diethyl ether (approximately 20 mL) was added to the resulting reaction solution, and the system was washed with water. After this, the organic layer was dried with sodium sulfate, and then filtered with celite. The solvent was then distilled off from the filtrate, after which the remaining liquid was refined by silica gel column chromatography using hexane as the developing solvent, which gave the targeted substance, in which n=3 in General Formula (5c), in the form of an oily substance (41 mg, isolation yield of 62%). After the reaction, it was confirmed by GC analysis that the yield of the target substance was 89%. The No compound expressed by General Formula (5d) was produced.

The product thus obtained was measured by $^1$H-NMR and HRMS, the results of which were as follows.

$^1$H-NMR (400 MHz, CDCl$_3$, ppm): δ 7.46 (d, J=5.5 Hz, 2H), 7.37 (d, J=5.5 Hz, 2H), 3.02 (m, 4H), 1.70-1.62 (m, 4H), 1.53-1.37 (m, 8H), 0.93 (t, J=7.3 Hz, 6H).

HRMS (EI): m/z 330.1469 (the value obtained by measurement with C$_{20}$H$_{26}$S$_2$ was 330.1476)

Working Example 6

Synthesis of 4,5-di(n-heptyl)benzo[2,1-b:3,4-b'] dithiophene

Everything was carried out in the same manner as in Working Example 5, except that 8-hexadecyne (53 mg (0.24 mmol)) was used instead of 6-dodecyne, which gave the targeted substance, in which n=5 in General Formula (5c), in the form of an oily substance (58 mg, isolation yield of 74%). After the reaction, it was confirmed by GC analysis that the yield of the target substance was over 99%. No compound expressed by General Formula (5d) was produced.

The product thus obtained was measured by $^1$H-NMR and HRMS, the results of which were as follows.

$^1$H-NMR (400 MHz, CDCl$_3$, ppm): δ 7.46 (d, J=5.5 Hz, 2H), 7.36 (d, J=5.5 Hz, 2H), 3.01 (m, 4H), 1.70-1.61 (m, 4H), 1.52-1.45 (m, 4H), 1.41-1.25 mm (m, 12H), 0.90 (t, J=7.0 Hz, 6H).

HRMS (EI): m/z 386.2168 (the value obtained by measurement with C$_{24}$H$_{34}$S$_2$ was 386.2102)

Comparative Example 1

Synthesis of 4,5-di(n-propyl)benzo[2,1-b:3,4-b'] dithiophene

The same reaction as in Working Example 1 was conducted, except that potassium carbonate (K$_2$CO$_3$, 83 mg (0.6 mmol)), which is a base other than an amine, was used instead of N,N-dicyclohexylmethylamine (Cy$_2$MeN), and the reaction time was changed to 8 hours. After the reaction, it was confirmed by GC and GC-MS analysis that the target substance, in which n=1 in General Formula (5c), had been produced at a yield of 54% in the reaction mixture. It was also confirmed that a by-product, in which n=1 in General Formula (5d), had been produced at a yield of 11%.

The by-product 4-(n-propyl)-5-(2-propenyl)benzo[2,1-b:3,4-b']dithiophene was measured by $^1$H-NMR and HRMS, the results of which were as follows.

$^1$H-NMR (400 MHz, CDCl$_3$, ppm): δ 7.54 (d, J=5.5 Hz, 1H), 7.47 (d, J=5.5 Hz, 1H), 7.38 (d, J=5.5 Hz, 1H), 7.32 (d, J=5.5 Hz, 1H), 6.82-6.76 (m, 1H), 5.98 (dq, J=15.8, 6.6 Hz, 1H), 3.04-2.90 (m, 2H), 2.01 (dd, J=6.4, 1.8 Hz, 3H), 1.72-1.64 (m, 2H), 1.03 (t, J=7.3 Hz, 3H).

HRMS (EI): m/z 272.0690 (the value obtained by measurement with C$_{16}$H$_{16}$S$_2$ was 272.0693)

The results obtained in Working Examples 1 to 6 and Comparative Example 1 are complied in Table 1.

TABLE 1

|  | Value of n in formulas | Amine | Base other than amine | Yield of compound of Gen. Form. (5c) (%) | Yield of compound of Gen. Form. (5d) (%) |
|---|---|---|---|---|---|
| Work. Ex. 1 | 1 | Cy$_2$MeN | — | >99 | 0 |
| Work. Ex. 2 | 1 | Bu$_3$N | — | >99 | 0 |
| Work. Ex. 3 | 1 | CyMe$_2$N | — | 92 | 0 |

TABLE 1-continued

|  | Value of n in formulas | Amine | Base other than amine | Yield of compound of Gen. Form. (5c) (%) | Yield of compound of Gen. Form. (5d) (%) |
|---|---|---|---|---|---|
| Work. Ex. 4 | 1 | i-Pr$_2$EtN | — | 88 | 0 |
| Work. Ex. 5 | 3 | Cy$_2$MeN | — | 89 | 0 |
| Work. Ex. 6 | 5 | Cy$_2$MeN | — | >99 | 0 |
| Comp. Ex. 1 | 1 | — | K$_2$CO$_3$ | 54 | 11 |

It can be seen from Table 1 that with Working Examples 1 to 6, in which the reaction was conducted in the presence of an amine, compared to Comparative Example 1, in which the reaction was conducted in the presence of K$_2$CO$_3$ instead of an amine, the compound of General Formula (5c) as the target substance was obtained at a better yield, and selectivity was far higher.

The invention claimed is:

1. A method for manufacturing a fused ring compound, wherein a compound expressed by the following Formula (2a) and a compound expressed by the following Formula (2b) are reacted in the presence of an amine and a metal complex catalyst, thereby obtaining a fused ring compound expressed by the following Formula (2c):

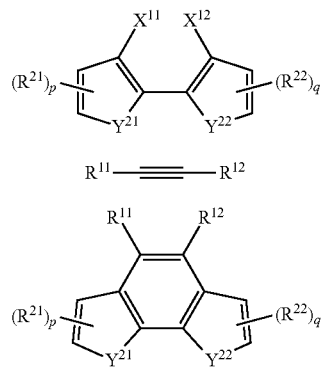

wherein $X^{11}$ and $X^{12}$ are each independently a hydrogen atom or a halogen atom, provided that at least one of $X^{11}$ and $X^{12}$ is a halogen atom; $R^{11}$ and $R^{12}$ are each independently a hydrogen atom, an alkyl group, an alkoxy group, an alkylthio group, an alkylamino group, an alkoxycarbonyl group, or a cyano group, provided that at least one of $R^{11}$ and $R^{12}$ is not a hydrogen atom; $R^{21}$ and $R^{22}$ are each independently a monovalent group; p and q are each independently an integer from 0 to 2; and $Y^{21}$ and $Y^{22}$ are divalent groups expressed by the following Formula (3a):

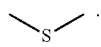

(3a)

2. The method for manufacturing a fused ring compound according to claim 1, wherein $R^{11}$ and $R^{12}$ are each independently a C$_1$ to C$_{20}$ alkyl group.

3. The method for manufacturing a fused ring compound according to claim 1, wherein at least one of $X^{11}$ and $X^{12}$ is an iodine atom.

4. The method for manufacturing a fused ring compound according to claim 1, wherein the amine is a trialkylamine.

5. The method for manufacturing a fused ring compound according to claim 1, wherein the metal complex catalyst is a metal complex catalyst containing Pd.

* * * * *